(12) United States Patent
Motta et al.

(10) Patent No.: US 6,524,290 B2
(45) Date of Patent: Feb. 25, 2003

(54) MULTIFUNCTIONAL ABSORBENT ARTICLE

(75) Inventors: Miriam Motta, Franklin Park, NJ (US); Jennifer L. Sturgeon, Long Valley, NJ (US); Yake Yu, East Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/738,034

(22) Filed: Dec. 15, 2000

(65) Prior Publication Data

US 2002/0138055 A1 Sep. 26, 2002

(51) Int. Cl.$^7$ .................................. A61F 13/15
(52) U.S. Cl. ..................... 604/385.01; 604/385.11
(58) Field of Search .......................... 604/317–402; 2/400–406

(56) References Cited

U.S. PATENT DOCUMENTS

| | | |
|---|---|---|
| 1,238,356 A | 8/1917 | Stokes |
| 2,331,271 A | 10/1943 | Gilchrist |
| 2,399,545 A | 4/1946 | Davis |
| 2,508,855 A | 5/1950 | Brown |
| 3,049,228 A | 8/1962 | Burnett |
| 3,071,138 A | 1/1963 | Garcia |
| 3,143,208 A | 8/1964 | Sizemore, Jr. |
| 3,183,910 A | 5/1965 | Patterson |
| 3,211,147 A | 10/1965 | Pherson et al. |
| 3,315,676 A | 4/1967 | Cooper |
| 3,411,504 A | 11/1968 | Glassman |
| 3,638,651 A | 2/1972 | Torr |
| 3,828,784 A | 8/1974 | Zoephel |
| 3,835,992 A | 9/1974 | Adams, IV |
| 3,885,566 A | 5/1975 | Jacob |
| 3,916,447 A | 11/1975 | Thompson |
| 3,943,930 A | 3/1976 | Schaar |
| 3,967,622 A | 7/1976 | Cepuritis |
| 4,097,943 A | 7/1978 | O'Connell |
| 4,194,507 A | 3/1980 | Ness et al. |
| 4,245,630 A | 1/1981 | Lloyd et al. |
| 4,327,732 A | 5/1982 | Thinnes |
| 4,427,737 A | 1/1984 | Cilento et al. |
| 4,505,704 A | 3/1985 | Roeder |
| 4,562,102 A | 12/1985 | Rabuse et al. |
| 4,596,570 A | 6/1986 | Jackson et al. |
| 4,597,759 A | 7/1986 | Johnson |
| 4,598,528 A | 7/1986 | McFarland et al. |
| 4,605,404 A | 8/1986 | Sneider |
| 4,770,298 A | 9/1988 | McFarland et al. |
| 4,772,499 A | 9/1988 | Greenway |
| 4,773,905 A | 9/1988 | Molee et al. |
| 4,946,454 A | 8/1990 | Schmidt |
| D368,519 S | 4/1996 | Harrison et al. |
| 5,704,929 A * | 1/1998 | Bien ..................... 604/385.1 |

FOREIGN PATENT DOCUMENTS

| | | |
|---|---|---|
| CH | 435 550 | 10/1967 |
| EP | 0241041 A | 10/1987 |
| FR | 2541247 A | 8/1984 |
| GB | 1331354 A | 9/1973 |
| GB | 2141396 A | 1/1986 |
| JP | 2019596 A | 1/1990 |
| WO | 92/10984 A | 7/1992 |

OTHER PUBLICATIONS

U.S. patent application Ser. No. 09/012,767, O'Donnell et al.

* cited by examiner

*Primary Examiner*—Jeanette Chapman

(57) ABSTRACT

An absorbent article that is adaptable for use with different types of underwear, the absorbent article having an absorbent core having a length and a width; a backsheet having a length and a width underlying the absorbent core; and a first perforation line positioned between a first portion of the absorbent article and a second portion of the absorbent article, whereby separation of the first portion from the second portion along the first perforation line provides at least one newly shaped absorbent article wherein the length or width of the absorbent core is shorter and the length or width of the backsheet layer is shorter.

16 Claims, 8 Drawing Sheets

MULTIFUNCTIONAL ABSORBENT ARTICLE

This invention relates to an absorbent article, such as pantiliners, sanitary napkins, and incontinence pads. More particularly, the present invention relates to absorbent articles that are adaptable for use with different types of underwear.

BACKGROUND OF THE INVENTION

Currently, absorbent articles for sanitary protection, such as, pantiliners, sanitary napkins, and incontinence pads must fit a variety of individual body shapes and sizes. In particular, women have an almost infinite variety of body shapes and muscle tone in the upper thigh region. A product that offers superior comfort, fit, and protection for one woman may be deficient for another woman due to her body shape and muscle tone.

The availability of different types of underwear also affects the choice of absorbent articles for sanitary protection. For example, conventional pantiliners and napkins are typically designed to be used with underwear having a full sized crotch portion, e.g., briefs and bikinis. However, such conventional pantiliners and napkins attach or fit poorly to underwear having an abbreviated crotch portion, e.g., thong-type or G-string. As a result, many women purchase multiple types of sanitary protection depending on the underwear they choose to wear.

U.S. Pat. No. 5,704,929 (Bien) discloses an absorbent article having removable portions that can reduce the dimensions of the article. The preferred embodiment is a pantiliner that can be adjusted in size by tearing the absorbent article along one or more perforation lines and removing the portions that lie outboard the perforation lines. The resultant pantiliner, however, is designed for conventional underwear having a full sized crotch portion and is not adaptable for thong-type underwear having an abbreviated crotch portion (conventional and thong-type underwear are further discussed below).

U.S. Pat. No. 4,596,570 (Jackson et al.) and U.S. Pat. No. 4,597,759 (Johnson) disclose sanitary napkins capable of being elongated. Jackson et al. unfolds pleats at the longitudinal ends and Johnson adds a second absorbent element to a first element. Neither, however, discloses absorbent articles that have a posterior portion that is narrower than the anterior portion and are appropriate for use with thong-type underwear.

U.S. Design Pat. No. D368,519 (Harrison et al.) discloses a pantiliner having a perforated section in the posterior portion. The embodiments shown have posterior portions that are narrower than the anterior portions.

As evident from the above, women often have the expense and bother of purchasing assorted sized products to meet their needs. Often, a woman compromises and chooses only one size even though that selection may be less than ideal.

What is needed, therefore, is an absorbent article that offers sanitary protection and can be comfortable under multiple circumstances, including use with various underwear styles.

SUMMARY OF THE INVENTION

This invention relates to an absorbent article that is adaptable for use with different types of underwear, the absorbent article having an absorbent core having a length and a width; a backsheet having a length and a width underlying the absorbent core; and a first perforation line positioned between a first portion of the absorbent article and a second portion of the absorbent article, whereby separation of the first portion from the second portion along the first perforation line provides at least one newly shaped absorbent article wherein the length or width of the absorbent core is shorter and the length or the width of the backsheet is shorter.

Additionally, the absorbent article may include a third portion that may be used as an interlabial device.

DETAILED DESCRIPTION OF THE INVENTION

The absorbent article of this invention is a multifunctional absorbent article that allows a user to adapt the absorbent article to a desired shape. The absorbent article can be worn with conventional underwear having a full sized crotch or adapted to a shape more appropriate to be worn with thong-type underwear having an abbreviated crotch. Sanitary protection, however, is not compromised by the absorbent article's change in shape.

Conventional pantiliners are those that include an anterior, i.e., body facing portion, and a posterior body portion, which are substantially the same width from lateral side to lateral side. Conventional pantiliners may or may not be contoured in midsection. Examples of conventional pantiliners are described in the discussion of first portion 10 below. Thong-type underwear generally requires that the anterior portion have a greater width than the posterior portion. Thong-type pantiliners are described as second portion 20 below. Generally, thong-type underwear has a crotch portion that narrows to a minimal width of material in the rear of the undergarment, in order to expose all or a significant portion of the buttocks. For purposes of the present disclosure, the term "thong-type underwear" includes thongs, G-strings, Rio-cut underwear, Brazilian cut underwear, and any underwear having an abbreviated crotch. In use, it is not necessary that the user position the anterior portion of the pantiliner such that it overlays the anterior portion of the underwear. Some users, in fact, often reverse the pantiliner such that the posterior portion of the pantiliner overlays the anterior portion of the underwear.

The Figures depict an absorbent article 5 having a first portion 10 and a second portion 20 according to the present invention. In the embodiment depicted in FIG. 1, the shape of absorbent article 5 is such that it will fit comfortably within the crotch area of conventional underwear having a full sized crotch. If the user desires, the first portion 10 can be separated from second portion 20 along a first perforation line 30. According to this embodiment of the present invention, separated second portion 20 is appropriate for with thong-type underwear having an abbreviated crotch.

Figure 1:
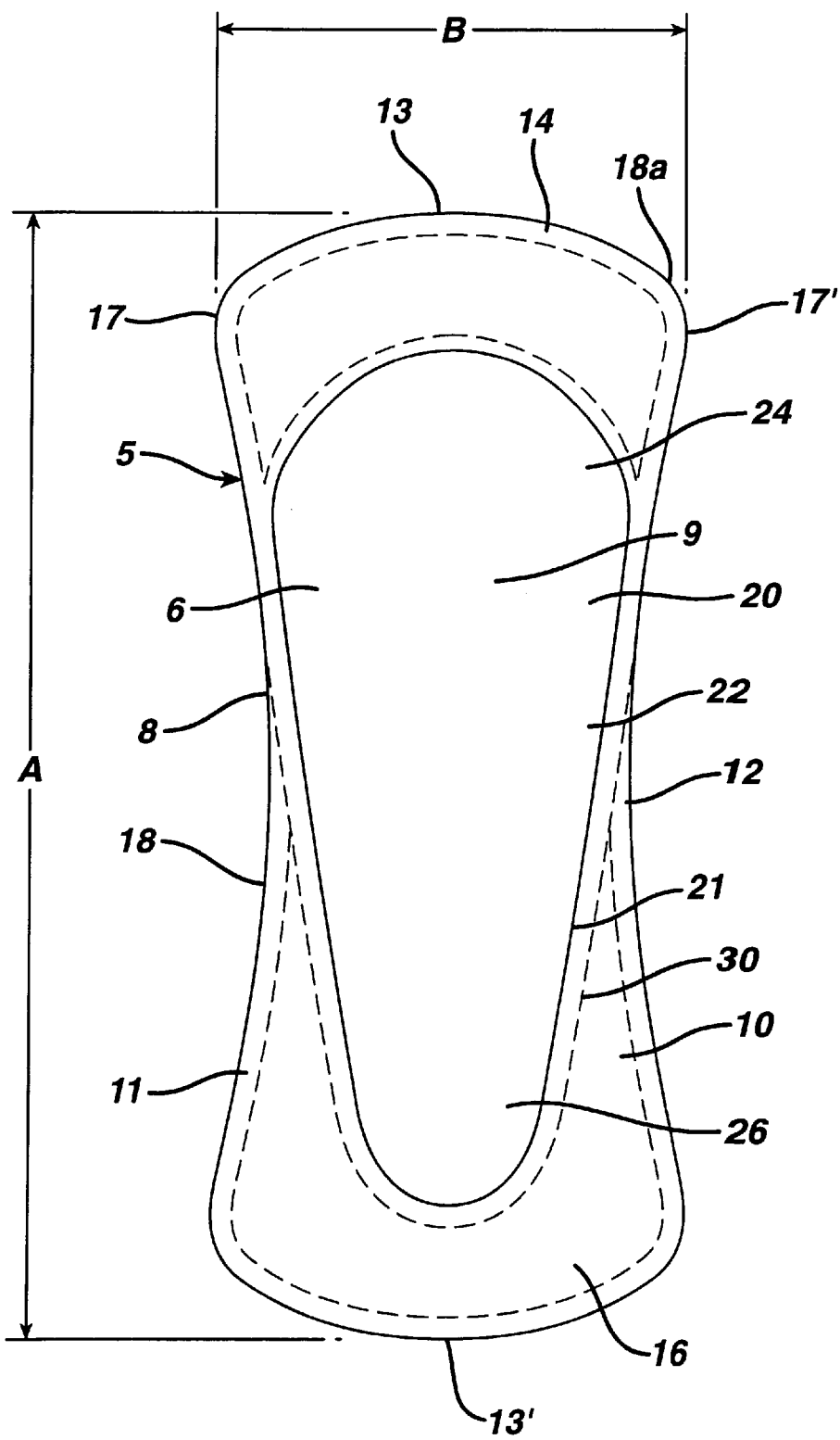
FIG. 1 is a top plan view of a pantiliner showing a first embodiment of the invention

In general, absorbent article 5 has absorbent core 6 and may optionally include backsheet 8 (shown in FIG. 1). Absorbent core 6 has length A taken from longitudinal end 13' to longitudinal end 13 and width B taken from lateral edge 17 to lateral edge 17'. Backsheet 8 has length A and width B. Optionally, cover 9 may overlay the absorbent core 6. In the present invention, first portion 10 and second portion 20 contain backsheet 8. In the preferred embodiment, the first portion contains the backsheet layer 8 and cover 9, while the second portion contains the absorbent core 6, backsheet 8 and cover 9. In an alternate embodiment shown in FIG. 5, each portion has the absorbent core 6, backsheet 8 and cover 9.

In first portion 10, midsection 12 connects anterior portion 14 and posterior portion 16. Outer perimeter edge 18 of first portion 10 is preferably sealed about the entire perimeter (sealing area 11). While the sealing area is optional and can be anywhere, it is preferred that sealing area 11 of first portion 10 be on outer edge 18. Methods of sealing include crimping and heating. Other methods known to those in the art may also be used. As seen in first portion 10 of FIGS. 1 and 2, anterior portion 14 and posterior portion 16 may have substantially square edges (18a in FIG. 1) or rounded edges (18b in FIG. 2).

In second portion 20, midsection 22 connects anterior portion 24 with posterior portion 26. As described previously, the width of the anterior portion 24 of the absorbent article is greater than the width of the posterior portion 26 of the second portion. The precise shapes of the anterior portion 24, midsection portion 22, and the posterior portion 26 of second portion 20 may vary as desired, so long as the maximum width of anterior portion 24 is greater than the width of posterior portion 26. For example, anterior portion 24 may have the overall shape of a triangle or may be round. Midsection 22 may be tapered and narrow at a substantially continuous rate along its length or may be biconcave in shape. Midsection 22 may also be a narrow, uniform band. The length of the absorbent article has a length of less than about 200 mm, more preferably, of from about 140 mm to about 195 mm. While the length of the absorbent article may be adapted to extend to the posterior portion of the underwear in use, the absorbent article may also be adapted to end near the midsection of the underwear in use.

Second portion 20 has sealing area 21. Perforation line 30 may be adjacent to sealing area 21.

Figure 2:
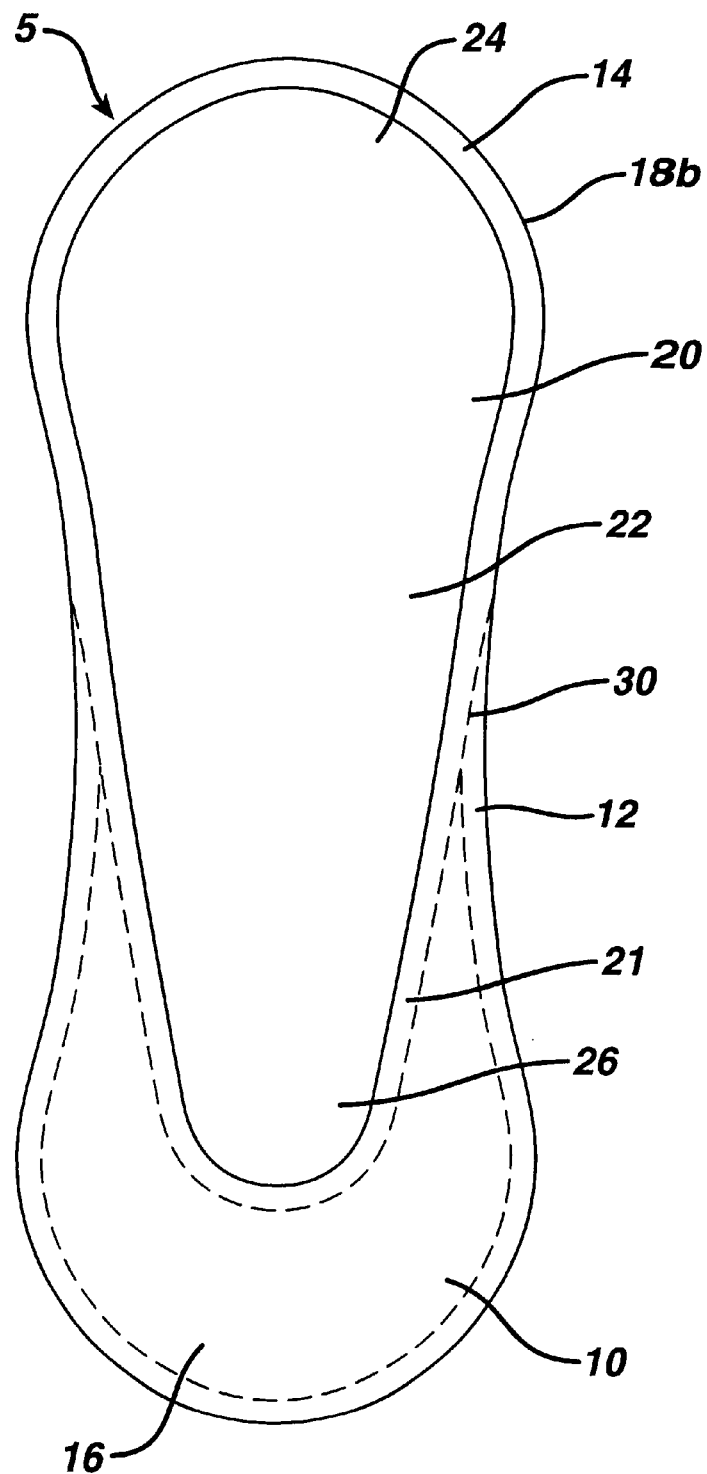
FIG. 2 is a top plan view of a pantiliner showing a second embodiment of the invention.

FIGS. 1–8 show various embodiments of absorbent article 5 having multifunctional uses. In FIG. 1, anterior portion 14 and posterior portion 16 of first portion 10 each have square corners. Second portion 20 is positioned equidistant from anterior portion 14 and posterior portion 16. FIG. 2 shows absorbent article 5 with anterior portion 14 and posterior portion 16 of first portion 20 having rounded shapes. Second portion 20 is in a more anterior location such that the greater width of the second portion is in the more useable area of the absorbent article, the portion of the absorbent article where the absorbent core is.

Figure 3:
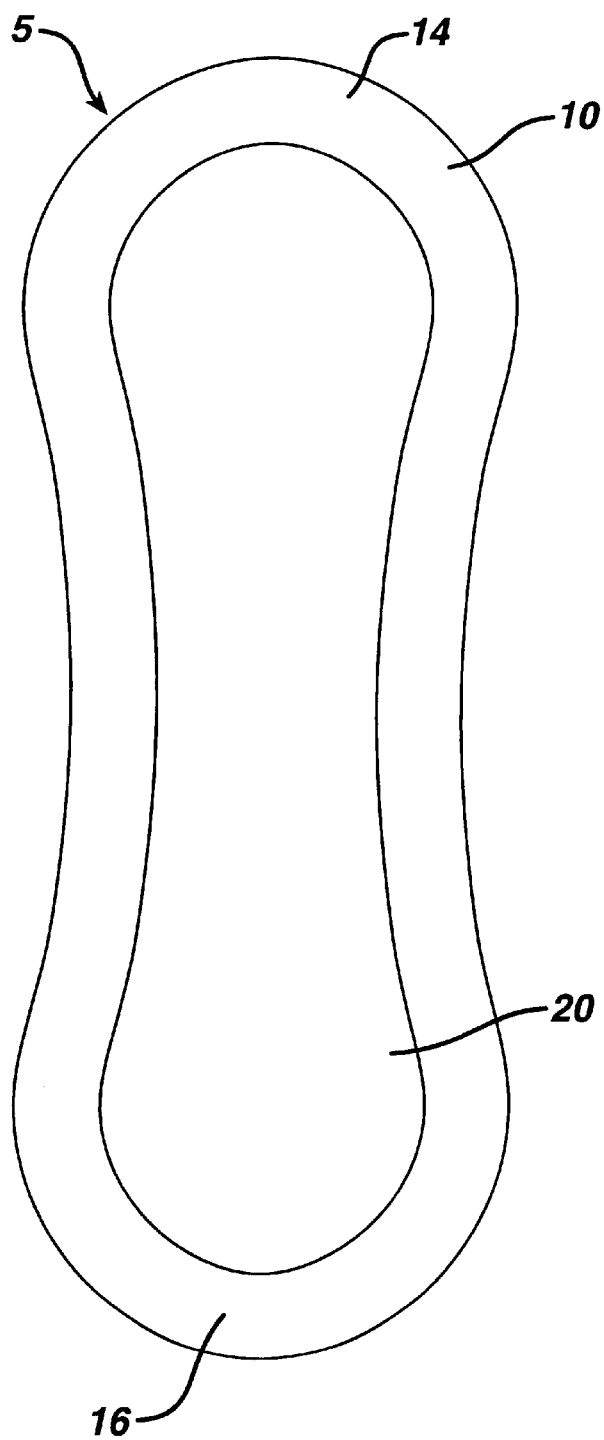
FIG. 3 is a top plan view of a pantiliner showing a third embodiment of the invention.
Figure 4:
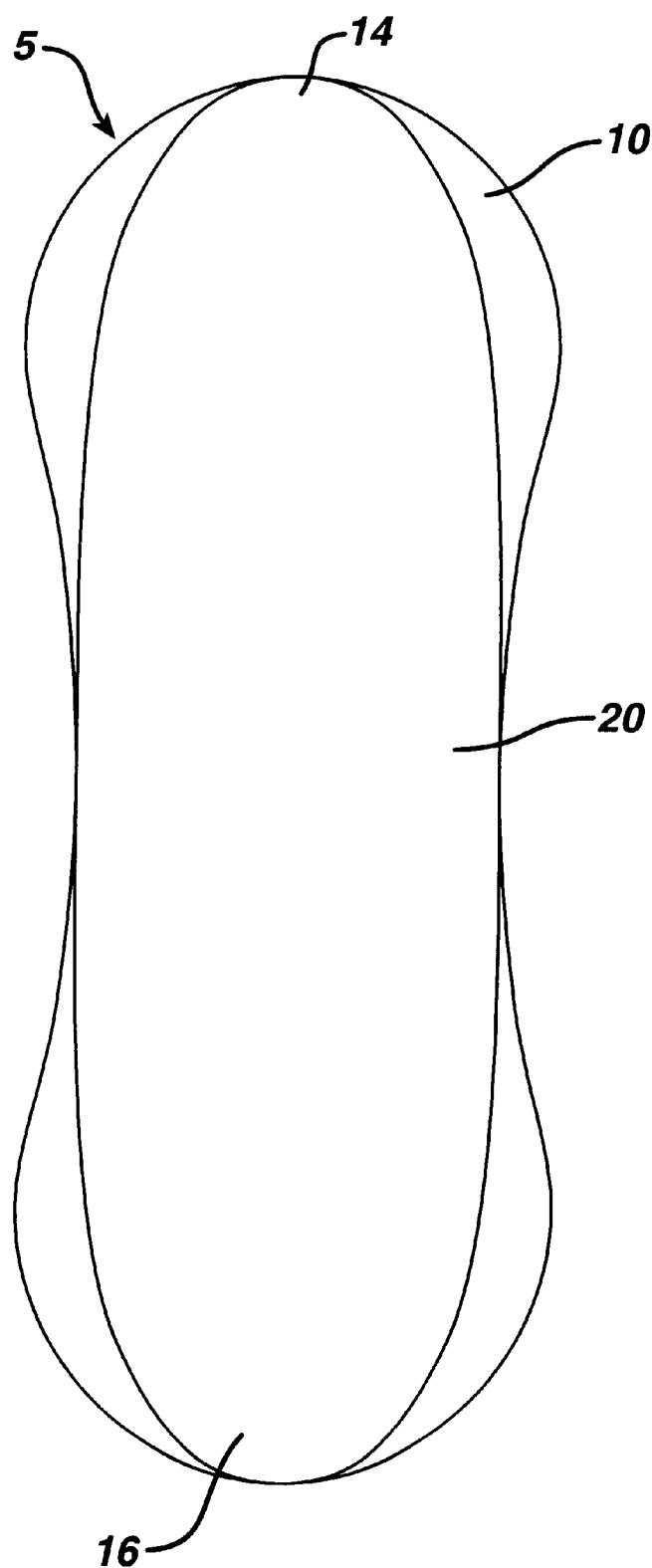
FIG. 4 is a top plan view of a pantiliner showing a fourth embodiment of the invention.
Figure 5:
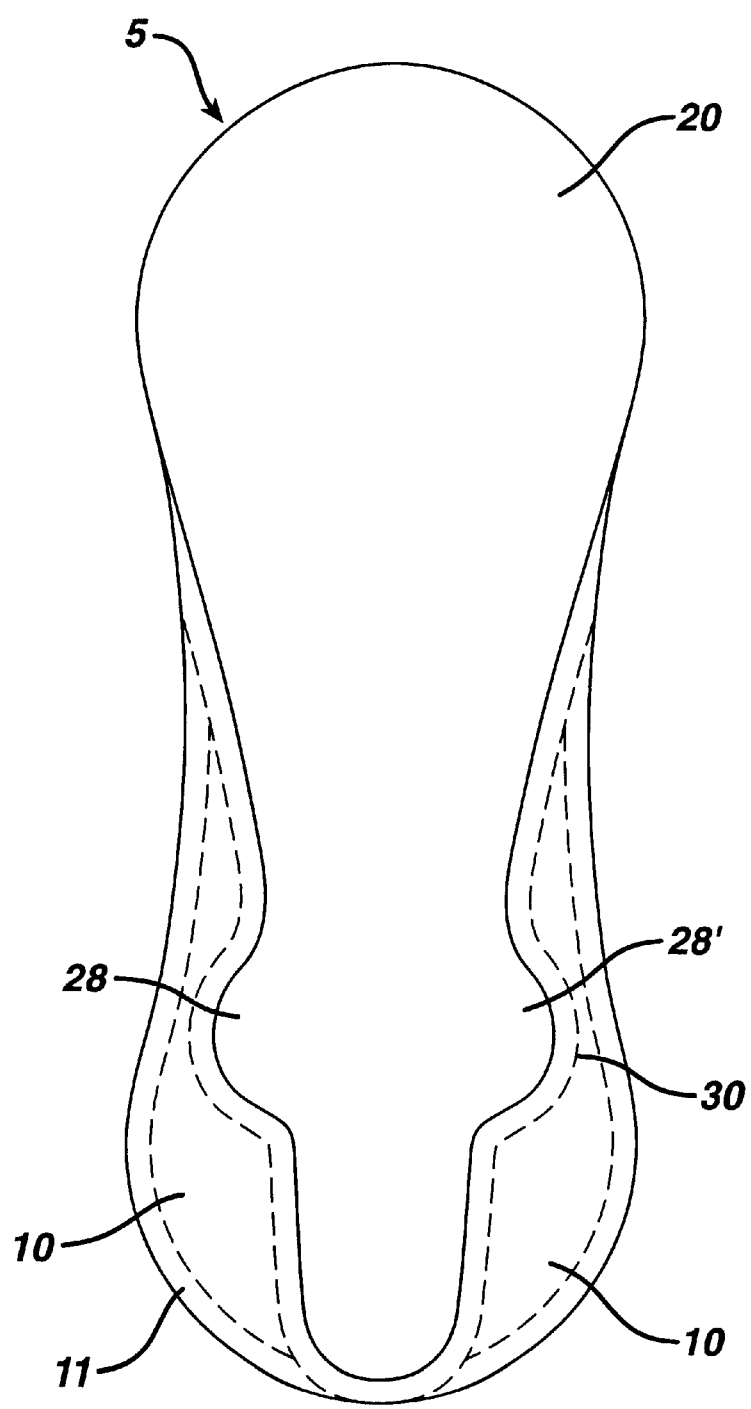
FIG. 5 is a top plan view of a pantiliner showing a fifth embodiment of the invention.

FIGS. 3 and 4 show alternate embodiments where first portion 10 is removed to leaving second portion 20, an absorbent article having a reduced area. FIG. 5 shows absorbent article 5 having second portion 20 that includes attachment tabs 28, 28', which can provide additional attachment to the thong-type underwear.

Figure 6:
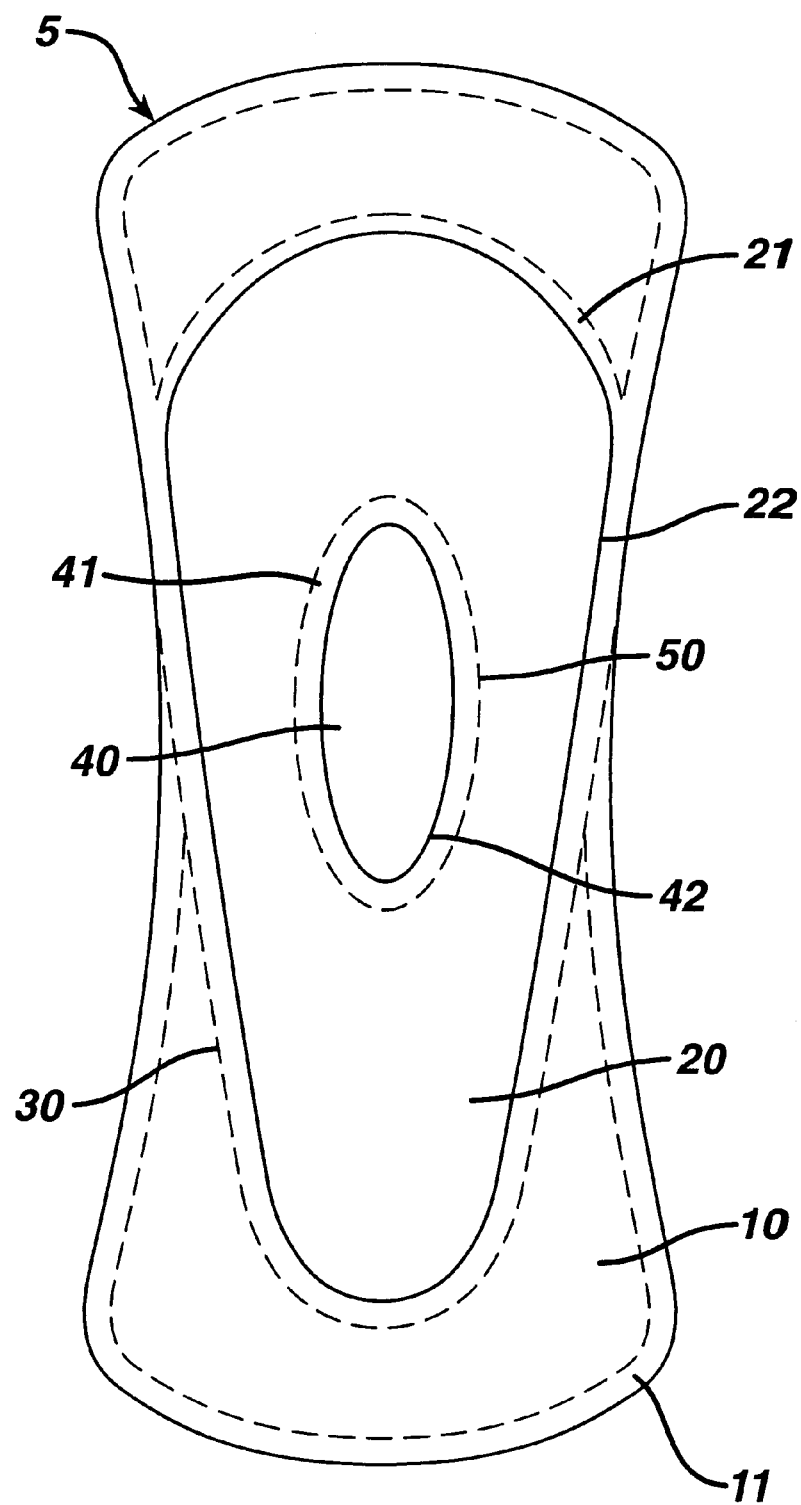
FIG. 6 is a top plan view of a pantiliner showing a sixth embodiment of this invention.
Figure 7:
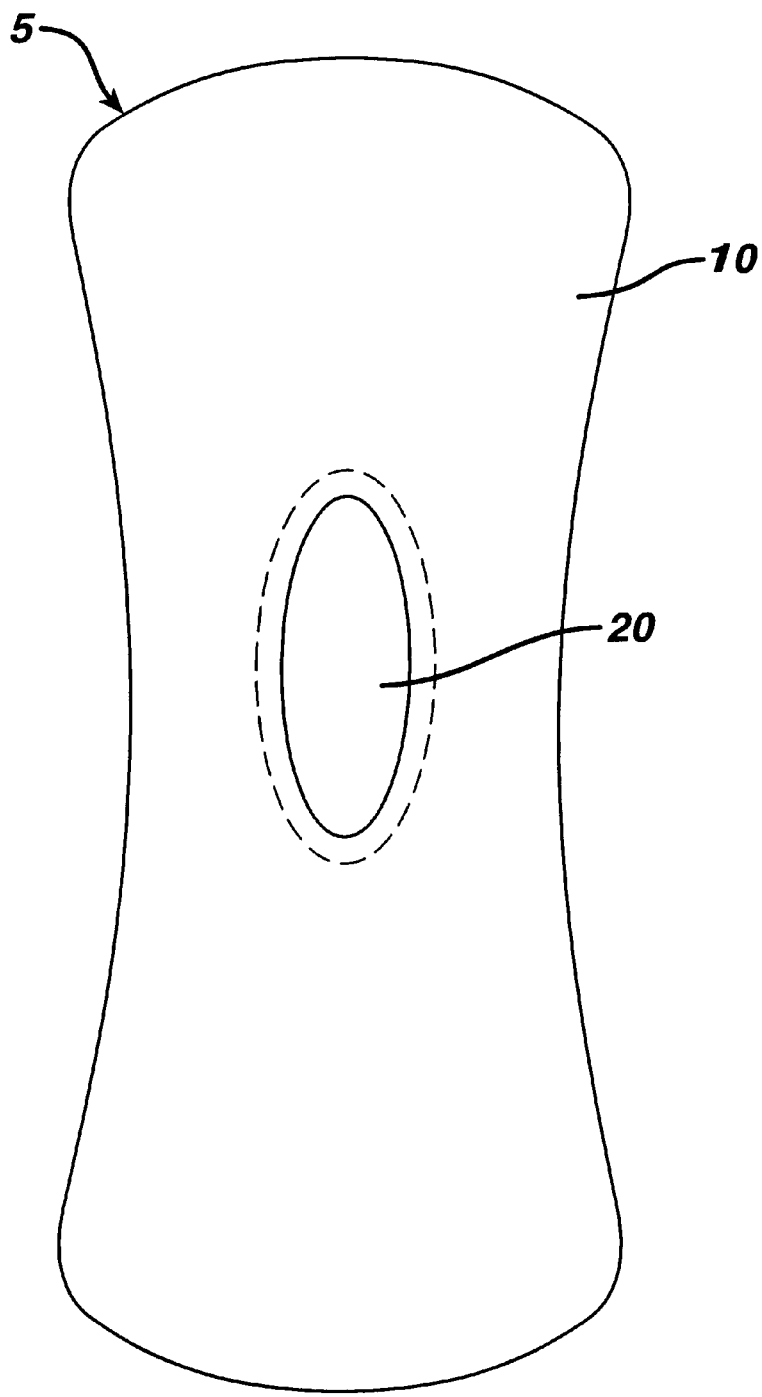
FIG. 7 is a top plan view of a pantiliner showing a seventh embodiment of this invention.

FIG. 6 shows absorbent article 5 having first portion 10, second portion 20, perforation line 30, and interlabial portion 40, which is removably attached to second portion 20 by interlabial perforation line 50. First portion 10 has sealing area 11, second portion 20 has sealing area 21 and interlabial portion 40 has sealing area 41. Interlabial portion 40 includes a layer of absorbent material, resulting in a protuberance or mound of material. If desired, interlabial portion 40 may be removed from second portion 20, which would allow second portion 20 or a combination of first portion 10 and second portion 20 to be used as a non-interlabial pantiliner. Alternately, FIG. 7 shows absorbent article 5 having first portion 10 and second portion 20, which is an interlabial portion. Additionally, the interlabial portion from FIGS. 6 and 7 may be used alone as an interlabial absorbent device.

In FIG. 6, perforation line 30 represents a line of cuts made through the absorbent article. The actual perforation may be completely through the absorbent article material or almost all the way through, which ever makes for an easy tear. If the perforation is to be made completely through the absorbent article, then it is important that the cuts be made completely through the absorbent core layer and optional backsheet layer. The perforation may be done when the product is complete, with or without the paper release strip. It is not necessary to cut the release paper, although the release paper may also be perforated. The cuts, however, must not compromise the strength of the absorbent article when securing the pantiliner to a garment. Additionally, the cuts must be close enough together to ensure easy and clean removal of the portion being removed. Perforation line 30 generally follows seal 21 of second portion 20. Interlabial perforation line 50 generally follows seal 41. It is not necessary for the cuts to be completely through the material of second portion 20. The depth of the cuts depends on the ease of separation desired. If, for example, a complete perforation is desired, it is important that the cuts be made completely through all layers, e.g., the absorbent core layer and the backsheet layer. During manufacturing, the timing of making perforation line 30 is not important. It is not necessary to perforate the release paper, if present, although the release paper may also be perforated. The perforation, however, must not compromise the strength of the absorbent article when the absorbent article is secured to a garment. Additionally, the perforation marks must be close enough together to ensure easy and clean removal of the first portion. Some women may prefer to leave the first portion 10 attached to the absorbent article 5 when wearing conventional underwear. Other women may prefer to remove first portion 10 and attach the absorbent article formed by second portion 20 to thong-type underwear. This adaptability of the present invention allows women to purchase a single product while allowing for complete sanitary protection regardless of the type of underwear they may choose to wear or the type of protection they may need on a particular day.

The choice of perforation methods is dependent on the materials and amount of cut required. Commonly used methods include knife cutting, ultrasonic cutting, laser, water jet, hot air jet, direct heat such as flame or convection heat, embossing, and sealing. A partially cutting knife will produce clean cuts through materials with parts of the perforation line not cut. For a sealing or embossing tool, the material would be crushed or fractured along the perforation line to form a stress concentrated area that tears easily away (the stress area may not actually be a perforated line but a weakened line). This weakness would be through the whole construction or through the non-paper release strip. Additionally, the materials used to make the layers may be precut before assembly of the absorbent article.

Figure 8:
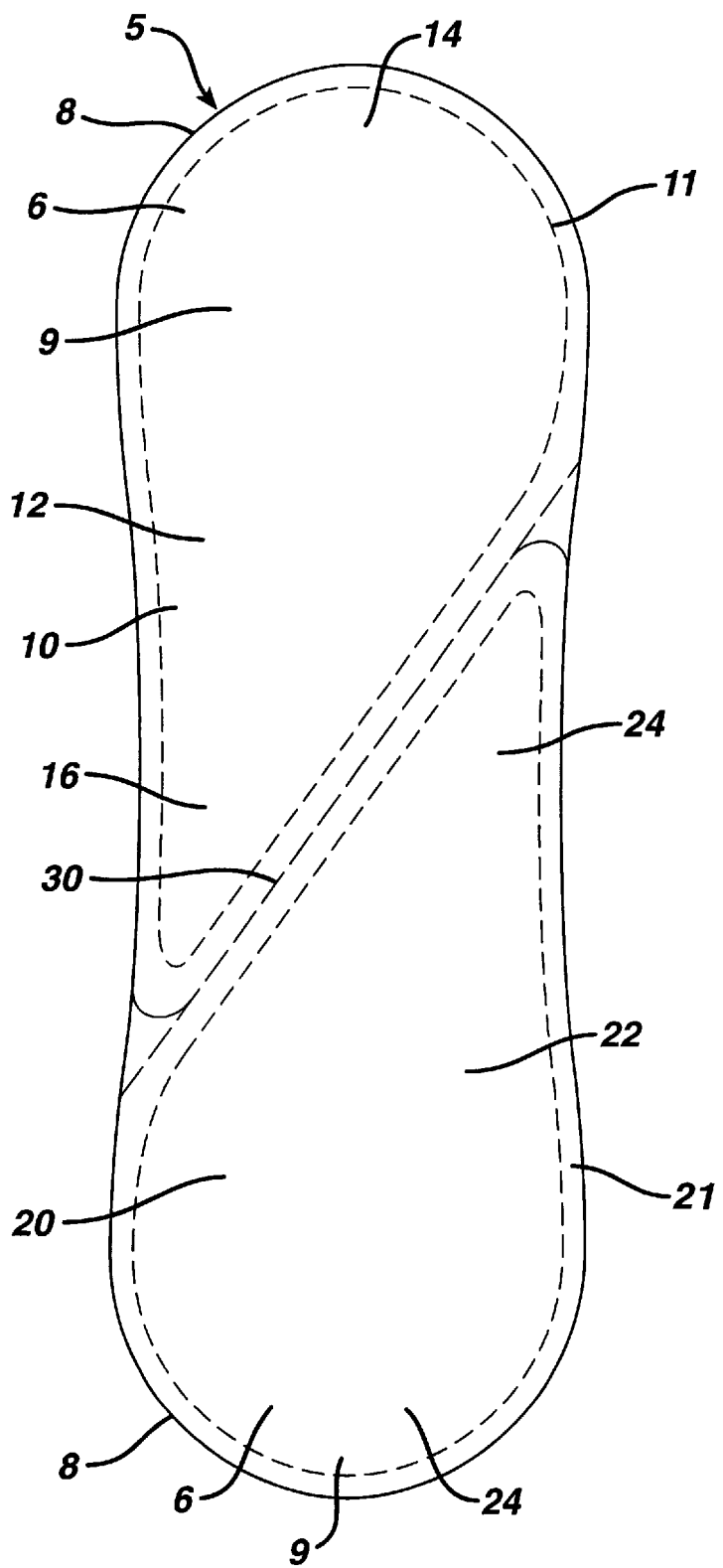
FIG. 8 is a top plan view of a pantiliner showing an eighth embodiment of this invention.

FIG. 8 shows an additional preferred embodiment wherein absorbent article 5 has first portion 10 and second portion 20 separated by perforation line 30. In this embodiment, unseparated absorbent article 5 may be used with conventional underwear or first portion 10 or second embodiment 20 may be used with thong-type underwear upon separation along perforation line 30.

First portion 10 has sealing area 11, anterior portion 14, posterior portion 16 and midsection 12. Second portion 20 has sealing area 21, anterior portion 24, posterior portion 26 and midsection 22. In second portion 20, the width of posterior portion 26 is larger than the width of anterior portion 24. Perforation line 30 separates sealing areas 21 and 11.

Absorbent article 5 has a body portion having absorbent core 6 and backsheet 8 underlying the absorbent core 6. That is, the garment-facing side of the absorbent core may have one or more layers of absorbent material including cellulose fibers, such as wood pulp, regenerated cellulose fibers, cotton fibers, acrylic fibers, polyvinyl alcohol fibers, peat moss, and superabsorbent polymers. Any one or combinations of these absorbent materials may be used to make absorbent core 6.

Backsheet 8 is substantially or completely impermeable to liquids, and its exterior forms the garment-facing surface of the absorbent article 5. Backsheet 8 may be made of any thin, flexible, body fluid impermeable material, such as a polymeric film or other nonwoven material having, for example, polyethylene, polypropylene, or cellophane. Alternatively, backsheet 8 may be a normally fluid permeable material that has been treated to be impermeable, such as impregnated fluid repellent paper, non-woven fabric material, or a flexible foam, such as polyurethane or cross-linked polyethylene. Additionally, the material used to form the backsheet may be blended into the absorbent core material during the initial manufacturing process. This results in one layer having absorbent and barrier characteristics.

The backsheet may be breathable, e.g., made of a film that is a barrier to liquids but permits vapors to transpire. Known materials for this purpose include nonwoven materials and microporous films in which microporosity is created by stretching an oriented film. Single or multiple layers of permeable films, fabrics, and combinations thereof that provide a tortuous path, and/or whose surface characteristics provide a liquid surface repellent to the penetration of liquids may also be used to provide a breathable backsheet.

The absorbent article may optionally have cover 9 overlaying the absorbent core 6, which is on the body-facing side of the pantiliner. The cover may be formed using any fluid pervious material that is comfortable against the skin and permits fluid to penetrate to the absorbent core, which retains fluid. The cover should retain little or no fluid to provide a relatively dry surface. A variety of cover materials are known in the art, and any of these may be used. For instance, the cover may be a fibrous non-woven fabric made of fibers or filaments of polymers, such as, polyethylene, polypropylene, polyester, or cellulose. Alternatively, the cover may be formed from an apertured polymeric film.

When absorbent article 5 has been separated to provide for a thong-type pantiliner, the pantiliner may be applied to the crotch of thong-type underwear by placing the garment-facing surface of the pantiliner against the inside surface of the crotch of the thong-type underwear. Strips of pressure sensitive adhesive may be applied to the garment-facing surface of the pantiliner to help maintain it in place. As used herein, the term pressure-sensitive adhesive refers to any releasable adhesive or releasable tenacious means. Preferred pressure sensitive adhesives include, for example, water-based adhesives, such as acrylate adhesives. Alternatively, the adhesive may be a hot melt rubber adhesive, two-sided adhesive tape or non-pressure sensitive adhesive.

A paper release strip, which has been coated, for example, with silicone on one side, may be applied to protect the strips of adhesive prior to use. The coating reduces adherence of the coated side of the release strip to the adhesive. The release strip can be formed from any suitable sheet-like material that, when coated, adheres with sufficient tenacity to the adhesive to remain in place prior to use but can be readily removed when the pantiliner is to be used.

The absorbent article of this invention may have other known materials, layers, and additives, such as transfer layers, foam layers, net-like layers, perfumes, medicaments, moisturizers, odor control agents, and the like, many examples of which are known in the art. The absorbent article can optionally be embossed with decorative designs using conventional techniques. The absorbent article may be made using conventional methods known to those skilled in the art.

While particular embodiments of the present invention have been illustrated and described, it is recognized to those skilled in the art that various other changes and modifications can be made without departing from the spirit and scope of the invention.

We claim:

1. An adaptable absorbent article comprising:
   (a) an absorbent core; and
   (b) a first perforation line positioned between a first portion of the absorbent article and a second portion of the absorbent article, wherein prior to separation of the first portion from the second portion along the first perforation line, the absorbent article is a conventional pantiliner and after such separation there is provided at least one thong-type pantiliner.

2. An absorbent article of claim 1, wherein the first portion comprises an outer perimeter having at least one longitudinal end and at least one lateral edge.

3. An absorbent article of claim 1, wherein said first portion comprises two longitudinal ends and two lateral edges.

4. An absorbent article of claim 1, wherein the thong-type pantiliner further comprises wings.

5. An absorbent article of claim 2, wherein the outer perimeter comprises a sealed portion.

6. An absorbent article of claim 1, wherein the second portion further comprises an outer perimeter having at least one longitudinal end and at least one lateral edge.

7. An absorbent article of claim 1, wherein the second portion comprises two longitudinal ends and two lateral edges.

8. An absorbent article of claim 7, wherein the outer perimeter comprises a crimp seal.

9. An absorbent article of claim 1, further comprising a third portion releasably attached to the second portion.

10. An absorbent article of claim 9, wherein the third portion is an interlabial absorbent article.

11. An absorbent article of claim 9, further comprising a second perforation line that is positioned between the second portion and the third portion.

12. An absorbent article of claim 9, wherein the third portion comprises an outer perimeter.

13. An absorbent article of claim 12, wherein the outer perimeter comprises a sealed portion.

14. An absorbent article of claim 1 wherein two thong-type pantiliners are provided after such separation.

15. An absorbent article that is adaptable for use with different types of underwear, the absorbent article comprising:
   (a) an absorbent core;
   (b) a backsheet having underlying the absorbent core; and
   (c) a first perforation line positioned between a first portion of the absorbent article and a second portion of the absorbent article, wherein separation of the first portion from the second portion along the first perforation line provides at least one thong-type pantiliner.

16. An adaptable absorbent article comprising:
   (a) an absorbent core; and
   (b) a first perforation line positioned between a first portion of the absorbent article and a second portion of the absorbent article, wherein prior to separation of the first portion from the second portion along the first perforation line, the absorbent article is a conventional pantiliner and after such separation there is provided at least one interlabial absorbent device.

* * * * *